(12) United States Patent
Wood et al.

(10) Patent No.: US 8,361,447 B2
(45) Date of Patent: Jan. 29, 2013

(54) COMPOSITION FOR PERMANENT SHAPING OF HUMAN HAIR

(75) Inventors: Jonathan Wood, Weinheim (DE); Alexandra Meuser, Weinheim (DE); Britta Punsch, Kesselsdorf (DE)

(73) Assignee: KPSS-KAO Professional Salon Services GmbH, Darmstadt (DE)

( * ) Notice: Subject to any disclaimer, the term of this patent is extended or adjusted under 35 U.S.C. 154(b) by 0 days.

(21) Appl. No.: 13/264,362

(22) PCT Filed: Apr. 23, 2010

(86) PCT No.: PCT/EP2010/002512
§ 371 (c)(1),
(2), (4) Date: Jan. 25, 2012

(87) PCT Pub. No.: WO2010/124820
PCT Pub. Date: Nov. 4, 2010

(65) Prior Publication Data
US 2012/0145176 A1 Jun. 14, 2012

(30) Foreign Application Priority Data
Apr. 27, 2009 (EP) .................................. 09005822

(51) Int. Cl.
*A61Q 5/06* (2006.01)
(52) U.S. Cl. .................... 424/70.1; 424/70.2; 424/70.14

(58) Field of Classification Search ................. 424/70.1, 424/70.2, 70.14
See application file for complete search history.

(56) References Cited

U.S. PATENT DOCUMENTS

| 4,459,284 A | * | 7/1984 | Azuma et al. ................ 424/70.5 |
| 4,935,230 A | | 6/1990 | Naito et al. |
| 5,116,608 A | | 5/1992 | Yoshioka et al. |

FOREIGN PATENT DOCUMENTS

| EP | 0 235 783 A | 9/1987 |
| EP | 0 361 391 A | 4/1990 |
| JP | 11 012138 A | 1/1999 |

OTHER PUBLICATIONS

International Search Reported dated Apr. 20, 2011.

* cited by examiner

*Primary Examiner* — Eisa Elhilo
(74) *Attorney, Agent, or Firm* — Norris McLaughlin & Marcus PA

(57) ABSTRACT

The present invention concerns a composition for the permanent shaping of human hair used both for the permanent waving of human hair with an excellent waving effect as well as for the straightening of either naturally or chemically curled hair comprising at least one dipeptide. Accordingly, the present invention is on a composition for permanent shaping hair based on at least one reducing agent and at least one dipeptide.

15 Claims, No Drawings

COMPOSITION FOR PERMANENT SHAPING OF HUMAN HAIR

This application is a 371 application of PCT/EP2010/002512 filed Apr. 23, 2010, which claims foreign priority benefit under 35 U.S.C. §119 of European Application No. 09005822.3 filed Apr. 27, 2009.

The present invention relates to a composition for the permanent shaping of human hair used both for the permanent waving of human hair with an excellent waving effect as well as for the straightening of either naturally or chemically curled hair comprising at least one dipeptide.

It is generally known that permanent waving is carried out in two steps, the reductive splitting of the cysteine disulfide bonds in the hair by a reducing agent, and the subsequent neutralization by application of an oxidizing agent, whereby the cysteine disulfide bonds are restored.

The reducing agent still has frequently been used is thioglycolic acid, also in form of the salts thereof, in particular its ammonium salt, although numerous other thio compounds have been proposed for this purpose, which, however, mostly did not succeed because of mainly toxicological reasons.

The compositions containing thioglycolates are customarily applied at a pH-value between 7 and 10, in particular 7.5 and 9.5.

Such compositions vary in their waving and/or straightening performance and, therefore, there is still need for further improvement. One of the major problems is varying efficiency of conventional permanent shaping compositions on hair having various level of damage in its lengths. In other words, hair towards the roots is mostly healthy, and towards the tips is mostly damaged. The problem is aggravated on chemically processed hair. The conventional compositions deliver good permanent shaping performance on healthy hair whereas the efficiency is relatively poor on damaged hair or vice versa. There is, therefore, need for permanent shaping compositions having efficient permanent shaping effect independent from the damage level.

The present invention starts from the task of providing a composition for the permanent shaping of human hair with excellent waving and straightening performance. Hair waved or straightened with composition disclosed herein looks and feels natural upon touching by hand. For waved hair it is especially important that the hair has excellent elasticity and bounce.

It has surprisingly been observed that a permanent shaping composition based on at least one reducing agent and further comprising at least one dipeptide has excellent straightening and waving effects and additionally hair either straightened or waved has improved elasticity, feels natural and softer upon touching.

Accordingly, the first object of the present invention is a composition for permanent shaping hair based on at least one reducing agent and further comprising at least one dipeptide.

With the term dipeptide, compounds with two amino acid moieties are meant.

Use of amino acids in permanent shaping compositions has been known. For example EP 791350 A1 discloses compositions for permanently waving hair comprising one or more amino acids. Similarly, DE 31 38 142 A1 is on permanent waving compositions comprising one or more amino acids for intensive waves. However, nothing is known in the literature on a composition comprising a dipeptide and a reducing agent for effectively permanent shaping human hair.

The dipeptide compounds according to the present invention comprise 2 amino acid moieties. In principal any dipeptide available either natural or synthetic are suitable for the purposes of the present invention. The synthetic ones are preferred. In one of the preferred embodiment of the present invention the amino acid moieties are selected from arginine, tyrosine, valine, tryptophan, alanine, cysteine, glycine, lysine, proline, hydroxyproline and histidine. The dipeptides according to the present invention may certainly be of two different amino acids but at the same time two of the same amino acids. In a further preferred embodiment of the present invention, the two amino acid moieties are of different amino acids when one of the amino acid moieties is glycine and more preferably are of two different amino acids.

Non-limiting examples to the suitable dipeptides are the ones commercially available and known with their INCI name as Dipeptide-1, Dipeptide-2, Dipeptide-3, Dipeptide-4, Dipeptide-5, Dipeptide-6, Dipeptide-7, Dipeptide-8, and carnosine. The most preferred is carnosine and is containing β-alanin and L-histidine.

Concentration of at least one dipeptide is in the range of 0.01 to 5%, preferably 0.05 to 3% and more preferably 0.1 to 2.5% and most preferably 0.2 to 1.5% by weight calculated to the total of reducing composition.

The permanent shaping compositions according to the invention comprise at least one reducing agent at a concentration of at least 0.5% by weight calculated to total composition. Preferred are thioglycolic acid and thiolactic acid as well as the salts thereof, in particular the ammonium and ethanolamine salts. Further useful thio compounds are in particular cysteine or the hydrochloride thereof, homocysteine, cysteamine, N-acetyl cysteine, thioglycerol, ethanediol monothioglycolate, 1,2-propyleneglycol monothioglycolate (see also WO-A 93/1791), 1,3-propanediol monothioglycolate or the isomer mixture resulting therefrom, 1,3-butanediol and 1,4-butanediol monothioglycolate and the isomer mixtures therefrom, polyethylene glycol, such as di-, tri- and tetraethyleneglycol monothioglycolates, glycerol monothiolactate and further thio acids and the esters thereof, as well as mixtures thereof.

The use of inorganic reducing sulfur compounds such as sodium hydrogen sulfite is basically also possible.

The total reduction agent content in the compositions according to the invention customarily amounts from 0.5 to 15%, preferably 1.0 to 12.5%, more preferably 1.5 to 12.5%, most preferably 2.0 to 12.5% by weight, calculated to total of reducing composition.

The permanent shaping compositions comprising reducing agents comprise, if necessary, alkalizing agents. Their quantity is dependent on the reducing agent and the desired pH-value of the composition. Reducing agent compositions preferably comprise 0.1% to 5%, in particular 0.5% to 2.5% by weight thereof, calculated to the total composition. Alkalizing agents preferred within the scope of the invention are ammonium carbamate, ammonia and/or ammonium(bi)carbonate, monoethanolamine and triethanolamine. It is desirable to adjust the pH-value between about 6.5 and 10.5, preferably about 7 to 9.5.

Permanent shaping compositions of the present invention preferably comprise additionally at least one cationic polymer. In principal suitable are all cationic polymers listed under the generic name "Polyquaternium" in the CTFA International Cosmetic Ingredient Dictionary. Preferred are Polyquaternium 2, Polyquaternium 4, Polyquaternium 5, Polyquaternium 6, Polyquaternium 7, Polyquaternium 10, Polyquaternium-11, Polyquaternium 16, Polyquaternium 22, Polyquaternium 28, Polyquaternium 39, and Polyquaternium-87.

The cationic polymers also include the quaternized products of graft polymers from organopolysiloxanes and polyethyl oxazolines described in EP-A 524 612 and EP-A 640 643. Such polymer is known with its CTFA name Polysilicone-9.

It should be noted that composition can comprise more than one cationic polymer and especially mixture of quaternized products of graft polymers from organopolysiloxanes and polyethyl oxazolines such as Polysilicone-9 and at least one compound known with the general CTFA name Polyquaternium.

Total concentration of cationic polymer is in the range from of 0.01 to 5%, preferably 0.01 to 3% more preferably 0.02 to 2% and most preferably 0.05 to 1% by weight calculated to total of reducing composition.

The permanent shaping compositions according to the invention are suited for use both for the permanent waving, i.e. curling of human hair and for the straightening, i.e. smoothing thereof.

The viscosity best suited for the permanent shaping compositions according to the invention proved to be in the range of 1 to 10,000 mPa·s, preferably 1 to 5,000 mPa·s, measured at 20° C. in a Brookfield viscosimeter (no. 5 spindle), whereas the viscosity suited for the straightening compositions is preferably higher in a range up to 50,000 mPa·s, preferably up to 30,000 mPa·s measured at 20° C. in a Brookfield viscosimeter (no. 5 spindle).

The viscosity is adjusted by addition of the appropriate amounts of thickening agents known per se, such as cellulose derivatives. Thickening may as well be realized by formulating a composition in form of an emulsion with the use of $C_{10}$-$C_{22}$-fatty alcohols, in mixture with long mono alkyl chain quaternary ammonium surfactants.

The permanent shaping compositions according to the present invention preferably comprise surfactants selected from anionic, nonionic, cationic and amphoteric ones. Their proportion ranges from 0.05% to 10%, in particular from 0.1% to 5% by weight, calculated to total composition.

Suitable anionic surfactants are especially the known alkyl ether sulfates and carboxylic acids, in particular in form of their alkali salts, as well as protein fatty acid condensates.

Suitable nonionic surfactants, which are preferred within the scope of the invention, are in particular $C_8$-$C_{18}$-fatty alcohol polyglycol ethers, fatty acid polyglycol esters, fatty acid alkanolamides, amineoxides, and especially $C_8$-$C_{18}$-alkyl polyglucosides.

Also possible is the incorporation of amphoteric surfactants, such as the known alkyl betaines, alkyl amido betaines, and alkyl amphoacetates.

Further according to a further preferred embodiment, permanent shaping compositions comprise at least one cationic surfactant according to general formula

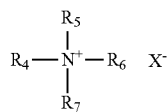

where $R_4$ is a saturated or unsaturated, branched or non-branched alkyl chain with 8-24 C atoms or

where $R_8$ is saturated or unsaturated, branched or non-branched alkyl chain with 7-21 C atoms and n has a typical value of 0-4 or

where $R_9$ is saturated or unsaturated, branched or non-branched alkyl chain with 7-21 C atoms and n has a typical value of 0-4, and $R_5$ is saturated or unsaturated, branched or non-branched alkyl chain with 1-24 C atoms or

where $R_8$ is saturated or unsaturated, branched or non-branched alkyl chain with 7-21 C atoms and n has a typical value of 0-4 or

where $R_9$ is saturated or unsaturated, branched or non-branched alkyl chain with 7-21 C atoms and n has a typical value of 0-4,
and $R_6$ and $R_7$ are independent from each other lower alkyl chain with 1 to 4 carbon atoms which may be substituted with one or more hydroxyl group, and X is chloride, bromide or methosulfate.

Concentration of cationic surfactant is in the range from 0.05% to 5%, preferably 0.1% to 2.5% by weight, calculated to total composition.

Suitable long-chain quaternary ammonium compounds are in particular cetyl trimethyl ammonium chloride, dimethyl dicetyl ammonium chloride, trimethyl cetyl ammonium bromide chloride, stearyl trimethyl ammonium chloride, dimethyl dihydrogenated tallow ammonium chloride, lauryl trimethyl ammonium chloride, etc.

One or more aminated silicones may be used in the compositions of the present invention. Suitable ones are any silicone compound having at least one amine group in its molecule. Well know and widely used example is amodimethicone available as an emulsion from various suppliers either as a cationic emulsion or as a non-ionic emulsion. Advantageously both types are suitable. Concentration varies in the range of 0.05 to 2.5% by weight calculated to total composition.

In another preferred embodiment of the present invention, suitable aminated silicone is amodimethicone and emulsified with Trideceth-5 and Trideceth-10. Such raw material is commercially available under the trade name Belsil ADM 8020 VP from Wacker Chemie.

Compositions of the present invention can comprise further at least one diamide compound. Preferred diamide compounds are according to the general structure

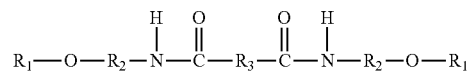

wherein $R_1$ is a linear or branched, saturated or unsaturated alkyl chain with 1 to 12 C atoms which may be substituted with hydroxy and/or alkoxy groups, preferably $R_1$ is linear or branched, saturated or unsaturated alkyl chain with 1 to 12 C atoms which may be substituted by 1 to 3 substituents selected from a hydroxy group and C1 to C6 alkoxy group, more preferably $R_1$ is a unsubstituted alkyl group with 1 to 12 C atoms, and alkyl group with 2 to 12 C atoms substituted by one or two hydroxyl groups, by one alkoxy group with 1 to 6 C atoms or by one hydroxyl and one alkoxy group with 2 to 6 C atoms, $R_2$ is linear or branched alkyl chain with 1 to 5 C atoms, preferably linear or branched alkyl chain with 2 to 5 C atoms and more preferably an alkyl chain with 2 to 3 C atoms, and $R_3$ linear or branched, saturated or unsaturated alkyl chain with 1 to 22 C atoms, preferably linear or branched, saturated or unsaturated alkyl chain with 11 to 22 C atoms.

Particularly preferred diamide compound is bis(methoxypropylamido) isodocosane and commercially available from Kao Corporation—Japan.

Concentration of diamide compounds in the compositions of the present invention is in the range of 0.001 to 5%, preferably 0.002 to 3% more preferably 0.005 to 2% and most preferably 0.01 to 1% by weight calculated to total composition.

Permanent shaping compositions of present invention can comprise additionally at least one organic solvent. Suitable organic solvents are 2-methyl-1,3-propanediol, mono and dialcohols or the ethers thereof, in particular mono-$C_1$-$C_3$-alkyl ether, ethanol, n-propanol, isopropyl alcohol, 1-methoxypropanol, 1-ethoxypropanol and ethoxydiglycol, diols and their esters 1,3- and 1,4-butanediol, diethyleneglycol and the monomethyl and monoethyl ether thereof, dipropylene glycol and the monomethyl and monoethyl ether thereof, glycerol, hexanetriol, ethyl carbitol, benzyl alcohol, benzyloxy ethanol, propylene carbonate, N-alkyl pyrrolidone, and urea or their mixture preferably in an amount from about 0.1% to 10% by weight, calculated to the total composition.

Permanent shaping composition of the present invention can comprise further ceramide type of compound such as cetyl-PG-hydroxyethylpalmitamide.

Further optional ingredient are sterols, especially the phytosterols as preferred hair restructuring agents. Especially preferred ones are of plant origin for example ergosterol, sitosterol, stigmasterol, fucosterol, brassicasterol, fungisterol, campesterol, zymosterol, ascosterol, cerevisterol, episterol, faecosterol, spinasterol. Among those phytosterols, the ones found in "Avocadin" which is the unsaponified fraction of the avocado oil is more preferred.

Optionally fatty acids of $C_{10}$ to $C_{22}$ may be incorporated into the compositions of the present invention at a concentration of preferably 0.01 to 2.5% by weight calculated to total composition.

Additionally, one or more natural oil component may be incorporated into the compositions of the present invention. Suitable are such as olive oil, almond oil, avocado oil, wheatgerm oil, ricinus oil or their mixture. Concentration of these natural oil ingredients should be 0.01 to 2.5%, preferably 0.01 to 1%, more preferably 0.05 to 0.5% by weight calculated to total composition.

Further additional compounds may be present in the permanent shaping compositions of the present invention is ubiqinone of the formula

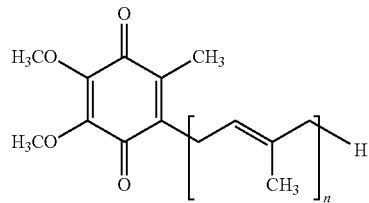

where n is a number between 1 and 10. Preferred ubiqinones are the ones where n is a number between 6 and 10 and especially preferred is Ubiqinone 50 where n is 10, also known as Coenzyme Q10. Concentration ubiqinone of the above formula in permanent shaping compositions of the present invention is from 0.0001 to 1%, preferably from 0.0002 to 0.75%, more preferably from 0.0002 to 0.5% and most preferably from 0.0005 to 0.5% by weight, calculated to total composition.

The compositions used according to the invention can naturally comprise all the substances customarily found in permanent shaping compositions, a list of which will not be given here, and are preferably present as solutions, gels with a higher or lower viscosity, emulsions or creams. They can be single-phase products or compositions packed into separate packaging which are united upon application, as they are disclosed, for example, in DE-C 43 04 828.

Composition of the present invention is used in a process for permanent waving wherein hair is washed or shampooed first and wound on the curlers, subsequently a reducing composition comprising at least one reducing agent, and at least one dipeptide is applied onto hair and after 1 to 45 min, preferably 1 to 30 min of processing time, depending on the hair strength, rinsed off from hair with tap water and an oxidizing composition comprising at least one oxidizing agent, preferably hydrogen peroxide or sodium bromate at a concentration of 0.5 to 10% by weight calculated to total of oxidizing composition, is applied onto hair and left on the hair 1 to 20 min and rinsed off and curlers are removed from hair. In cases where additional conditioning composition is required this may as well be applied after finishing the process as described above.

In another process as described above the curlers are removed after rinsing off the reducing agent and before applying the oxidizing agent.

Further in another process, after rinsing off the reducing agent from hair, an intermediate treatment composition is applied onto hair and without rinsing off, but after removing the excess amount of intermediate treatment with a towel, oxidizing composition is applied and at the end of the processing they are rinsed off from hair and curlers are removed from hair.

It has further been found out that the use of dipeptide in the intermediate treatment composition improves the permanent shaping of hair as well in terms of curl appearance and natural look and feel of hair. Therefore, in another preferred form of the present invention, permanent shaping of hair is carried out with a process wherein hair is washed or shampooed first and subsequently a composition comprising reducing agent, at least one dipeptide is applied onto hair and after 1 to 45 min, preferably 1 to 30 min of processing time, depending on the hair strength, rinsed off from hair with tap water and an intermediate treatment composition comprising at least one dipeptide is applied and without rinsing off an oxidizing composition comprising at least one oxidizing agent, preferably hydrogen peroxide or sodium bromate at a concentration of 0.5 to 10% by weight calculated to total of oxidizing composition, is applied onto hair and left on the hair 1 to 20 min and rinsed off. In cases where additional conditioning composition is required this may as well be applied after finishing the above process. In case of permanent waving hair in the above process curlers are put onto hair before application of reducing composition and taken off from hair before application of oxidizing composition or after application of the oxidizing agent or during processing of the oxidizing composition.

The intermediate treatment composition has a pH value between 2.5 to 6, preferably 3 to 5.5 and most preferably 3 to 5.

A straightening process may also be carried out in a different way wherein hair is washed and/or shampooed and dried and reducing composition comprising at least one reducing compound and at least one dipeptide is applied onto dry hair and processed for 5 to 60 min, preferably 5 to 45 min and rinsed off with water and dried and the dry hair physically straighten with hot iron at a temperature of 130 to 210° C. and subsequently an oxidizing composition comprising at least one oxidizing agent, preferably hydrogen peroxide or sodium bromate at a concentration of 0.5 to 10% by weight calculated to total of oxidizing composition, is applied onto hair and left on the hair 1 to 20 min and rinsed off from hair.

Present invention is also on a kit for permanent shaping hair comprising a first product containing a composition comprising at least one reducing compound and at least one dipeptide and a second product containing a composition comprising at least one oxidizing agent and optionally a third product comprising at least one dipeptide and having an acidic pH value, preferably between 2.5 and 6.

The following examples are to illustrate the invention, but not to limit it.

EXAMPLE 1

| Ammonium thioglycolate (60%) | 21.3 (% by wt.) |
| --- | --- |
| 1,3-butylene gylcol | 3.0 |
| Carnosine | 0.1 |
| PEG-40-Hydrogenated castor oil | 0.7 |
| Perfume | 0.4 |
| Ammonia, 25% | ad pH 8.3 |
| Water | ad 100.0 |

With the above composition, hair comprising parts with various level of damaged was permanently waved. First the above composition was applied and processed for about 15 minutes, rinsed and neutralized for about 8 minutes with a customary 2.5% $H_2O_2$ composition. Homogeneous wave appearance was obtained. Exclusion of carnosine resulted in less homogeneous perm appearance.

A comparative composition was prepared comprising no carnosine. Hair was waved according to the above described process. It was observed that the composition according to the invention resulted in far better waves which were homogeneous and had improved elasticity and especially hair felt softer upon touching and had excellent elasticity.

EXAMPLE 2

| Ammonium thioglycolate (60%) | 20 (% by wt.) |
| --- | --- |
| Ammonium hydrogen carbonate | 4.0 |
| 1,3-butylene gylcol | 3.0 |
| Carnosine | 0.1 |
| Polyquaternium-16 | 0.3 |
| PEG-40-Hydrogenated castor oil | 0.7 |
| Perfume | 0.4 |
| Ammonia, 25% | ad pH 8.3 |
| Water | ad 100.0 |

With this composition the hair was permanently waved. First the above composition was applied and processed for about 15 minutes, rinsed and neutralized for about 8 minutes with a customary 2.5% $H_2O_2$ composition. Homogeneous wave appearance was obtained. Exclusion of carnosine resulted in less homogeneous perm appearance.

EXAMPLE 3

| Ammonium thioglycolate (60%) | 15.0 (% by wt.) |
| --- | --- |
| Ammonium hydrogen carbonate | 2.5 |
| Ceteth-20 | 0.7 |
| Cetrimonium chloride | 0.5 |
| 1,3-butylene gylcol | 0.5 |
| Carnosine | 0.1 |
| Polyquaternium-6 | 0.8 |
| Perfume | 0.4 |
| Ammonia, 25% | ad pH 8.0 |
| Water | ad 100.0 |

The permanent wave achieved with this composition was similar to the one obtained with the composition according to Example 1.

Exclusion of carnosine led to waves with substantially weaker contours.

EXAMPLE 4

| Ammonium thioglycolate (60%) | 0.9 (% by wt.) |
| --- | --- |
| Cystein hydrochloride | 5.7 |
| Ammonium hydrogen carbonate | 1.5 |
| Cetrimonium chloride | 0.5 |
| 1,3-butylene gylcol | 0.5 |
| Diamide compound* | 0.03 |
| Carnosine | 0.1 |
| Polysilicone-9 | 0.3 |
| Coenzyme Q10 | 0.05 |
| Oleic acid | 0.05 |
| Perfume | 0.4 |
| Ammonia, 25% | ad pH 9.8 |
| Water | ad 100.0 |

*Bis (methoxypropylamido) isodocosane

The permanent wave achieved with this composition was similar to the one obtained with the composition according to Example 1.

Exclusion of carnosine led to substantially weaker waves.

EXAMPLE 5

A permanent waving product consisting of two compositions A and B, filled into a two-chamber packaging, the chambers of which were kept separate until application, was prepared by destruction of the separating wall and applied onto human hair rolled onto curlers. The hair was rinsed after about fifteen minutes processing and neutralized for about five minutes with a 2.5% $H_2O_2$ neutralizer composition, rinsed again, shampooed and dried.

An expressive, even, intensive permanent wave was obtained.

An identical treatment which had no carnosine showed a visibly inferior wave.

Composition A:

| Ammonium hydrogen carbonate | 4.5 (g) |
| --- | --- |
| Carnosine | 0.1 |
| Polyquaternium-87 | 0.5 |

-continued

| | |
|---|---|
| PEG-65-Hydrogenated castor oil | 0.8 |
| Isopropyl alcohol | 1.5 |
| Ethoxydiglycol | 2.0 |
| Cocoamidopropyl betaine | 1.0 |
| Perfume | 0.3 |
| Coenzyme Q10 | 0.05 |
| Turbidifying agent | 0.5 |
| Ammonia, 25% | ad pH 8.4 |
| Water | ad 72.0 |

Composition B:

| | |
|---|---|
| Ammonium thioglycolate, 70% | 18.0 (g) |
| Thiolactic acid | 2.0 |
| 2-Methyl-1,3-propanediol | 0.5 |
| Ammonia, 25% | ad pH 5.5 |
| Water | ad 28.0 |

After mixing of both compositions a ready-to-use product with a pH-value of 7.4 was obtained.

EXAMPLE 6

Intermediate Treatment Composition

| | |
|---|---|
| Magnesium sulfate | 10.0 |
| PEG-40 Hydrogenated castor oil | 0.5 |
| Poyquaternium-16 | 0.2 |
| Water | q.s. to 100 |

The above composition had a pH of 4.10.

Hair was waved with the composition of Example 1 according to the process disclosed therefore wherein the above composition was applied onto hair after the reducing composition was rinsed off from hair and oxidizing composition was applied onto hair. It was observed that homogeneous, softer hair with excellent elasticity was obtained.

In another trial, carnosine was included into the above intermediate composition. It was observed that the effects are more pronounced especially in the waving efficiency and curl elasticity.

EXAMPLE 8

Straightening Composition

| | |
|---|---|
| Thioglycolic acid | 8.0 (% by wt.) |
| $C_{16}$-$C_{22}$-Fatty alcohol mixture | 3.5 |
| Oleth-50 | 2.5 |
| Laureth-23 | 1.5 |
| Carnosine | 0.3 |
| Polyquaternium-6 | 0.5 |
| Ethanol | 5.0 |
| Perfume | 0.6 |
| Monoethanolamine | ad pH 9.3 |
| Water | ad 100.0 |

This composition constitutes an effecting smoothing composition for kinky hair.

The invention claimed is:

1. The composition for the permanent shaping of human hair wherein it comprises at least one reducing agent and at least one dipeptide.

2. The composition according to claim 1, wherein the reducing agent is selected from thioglycolic acid, thiolactic acid and their salts, cystein and its hydrochloride salt, acetylcystein, glycerylthioglycolate and thioglycolic acid esters.

3. The composition according to claim 1, wherein at least one dipeptide is selected from synthetic or natural ones.

4. The composition according to claim 1, wherein the amino acid moeties of dipeptide are selected from arginine, tyrosine, valine, tryptophan, alanine, cysteine, glycine, lysine, proline, hydroxyproline and histidine.

5. The composition according to claim 1, wherein it comprises at least one dipeptide at a concentration of 0.01 to 5% by weight calculated to total of reducing composition.

6. The composition according to claim 1, wherein at least one dipeptide is selected from Dipeptide-1, Dipeptide-2, Dipeptide-3, Dipeptide-4, Dipeptide-5, Dipeptide-6, Dipeptide-7, Dipeptide-8, and carnosine.

7. The composition according to claim 1, wherein it comprises at least one alkalizing agent.

8. The composition according to claim 1, wherein it comprises at least one cationic polymer, preferably selected from Polyquaternium 2, Polyquaternium 4, Polyquaternium 5, Polyquaternium 6, Polyquaternium 7, Polyquaternium 10, Polyquaternium-11, Polyquaternium 16, Polyquaternium 22, Polyquaternium 28, and Polyquaternium 39, Polyquaternium-87 and quaternized products of graft polymers from organopolysiloxanes and polyethyl oxazolines.

9. The composition according to claim 1, wherein it comprises at least one surfactant selected from anionic, nonionic, cationic and amphoteric ones at a concentration of 0.05 to 10% by weight, calculated to total composition.

10. The composition according to claim 1, wherein it comprises at least one organic solvent at a concentration of 0.1 to 10% by weight, calculated to total composition.

11. The composition according to claim 1, wherein it comprises at least one ubichinone of the formula

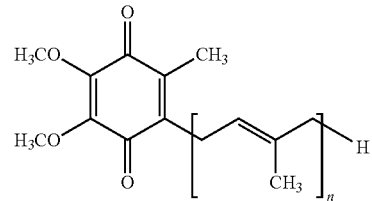

where n is a number between 1 and 10, and/or at least one compound according to general formula

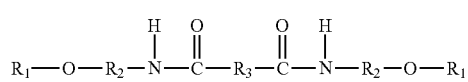

wherein $R_1$ is a linear or branched, saturated or unsaturated alkyl chain with 1 to 12 C atoms which may be substituted with hydroxy and/or alkoxy groups, preferably $R_1$ is linear or branched, saturated or unsaturated alkyl chain with 1 to 12 C atoms which may be substituted by 1 to 3 substituents selected from a hydroxy group and $C_1$ to $C_6$ alkoxy group, more preferably $R_1$ is a unsubstituted alkyl group with 1 to 12 C atoms, and alkyl group with 2 to 12 C atoms substituted by one or two hydroxyl groups, by one alkoxy group with 1 to 6 C atoms or by one hydroxyl and one alkoxy group with 2 to 6 C atoms, $R_2$ is linear or branched alkyl chain with 1 to 5 C atoms, and $R_3$ linear or branched, saturated or unsaturated alkyl chain with 1 to 22 C atoms.

12. The composition according to claim 1, wherein it has a pH in the range of 6.5 to 10.5.

13. The process for permanent waving hair wherein hair is washed or shampooed first and wound on curlers and subsequently a composition according to claim 1 is applied onto hair and at the end of the 1 to 45 min, rinsed off from hair with tap water and an oxidizing composition comprising at least one oxidizing agent, selected from the group consisting of hydrogen peroxide or sodium bromate at a concentration of 0.5 to 10% by weight calculated to total of oxidizing composition, is applied onto hair and left on the hair 1 to 20 min and rinsed off and curlers are removed from hair.

14. The process according to claim 12, wherein after rinsing off the reducing agent from hair, an intermediate treatment composition optionally comprising at least one dipeptide is applied onto hair and without rinsing off and after removal of the excess amount with towel, an oxidizing composition is applied and at the end of the processing they are rinsed off from hair.

15. A kit for permanent shaping human hair wherein it comprises a first product comprising a composition according to claim 1, a second product comprising a composition comprising at least one oxidizing agent and optionally a third product comprising a composition comprising at least one dipeptide and having pH between 2.5 and 6.

* * * * *